(12) United States Patent
Ip et al.

(10) Patent No.: US 6,652,530 B2
(45) Date of Patent: Nov. 25, 2003

(54) FIXATION DEVICE

(75) Inventors: Wing-Yuk Ip, Hong Kong (CN); Ting-Lai Lau, Hong Kong (CN)

(73) Assignee: The University of Hong Kong (HK)

( * ) Notice: Subject to any disclaimer, the term of this patent is extended or adjusted under 35 U.S.C. 154(b) by 63 days.

(21) Appl. No.: 09/956,930

(22) Filed: Sep. 19, 2001

(65) Prior Publication Data

US 2003/0055429 A1 Mar. 20, 2003

(51) Int. Cl.$^7$ .............................................. A61B 17/56
(52) U.S. Cl. ................................................... 606/69
(58) Field of Search ........................... 606/69, 60, 70, 606/71, 72, 73, 74

(56) References Cited

U.S. PATENT DOCUMENTS

| | | | | |
|---|---|---|---|---|
| 4,364,382 A | * | 12/1982 | Mennen | 606/69 |
| 4,565,193 A | * | 1/1986 | Streli | 606/69 |
| 4,573,458 A | * | 3/1986 | Lower | 606/69 |
| 4,651,724 A | * | 3/1987 | Berentey et al. | 606/69 |
| 5,015,248 A | * | 5/1991 | Burstein et al. | 606/74 |
| 5,718,705 A | * | 2/1998 | Sammarco | 606/69 |
| 5,779,706 A | | 7/1998 | Tschakaloff | |
| 5,797,916 A | * | 8/1998 | McDowell | 606/74 |
| 6,093,188 A | | 7/2000 | Murray | |
| 6,096,040 A | * | 8/2000 | Esser | 606/69 |
| 6,221,073 B1 | * | 4/2001 | Weiss et al. | 606/60 |
| 6,283,969 B1 | * | 9/2001 | Grusin et al. | 606/69 |

FOREIGN PATENT DOCUMENTS

| DE | 196 36 733 | 9/1996 |
|---|---|---|

OTHER PUBLICATIONS

International Search Report dated May 9, 2003.

* cited by examiner

Primary Examiner—Pedro Philogene
(74) Attorney, Agent, or Firm—Dickstein, Shapiro, Morin & Oshinsky, LLP.

(57) ABSTRACT

The present invention relates to a fixation device for internally fixing fractures. The fixation device has an elongated support plate and a transverse plate and a fin member extending transversely from the elongated support plate. The elongated support plate and the transverse plate define a plurality of holes for receiving fixing elements to mount the fixation device onto a bone. The holes can be so located that the fixing elements can prevent the fixation device from rotating relatively to the bone after the fixation device is mounted onto the bone. Additionally, the fin member is formed to be more flexible than the transverse plate. Thereby, the fin member can be bent to conform to the contour of the bone for fixing or stabilizing a fractured fragment. As a result, the fixation device can both support the injured bone and fix/stabilize the fractured fragment.

19 Claims, 1 Drawing Sheet

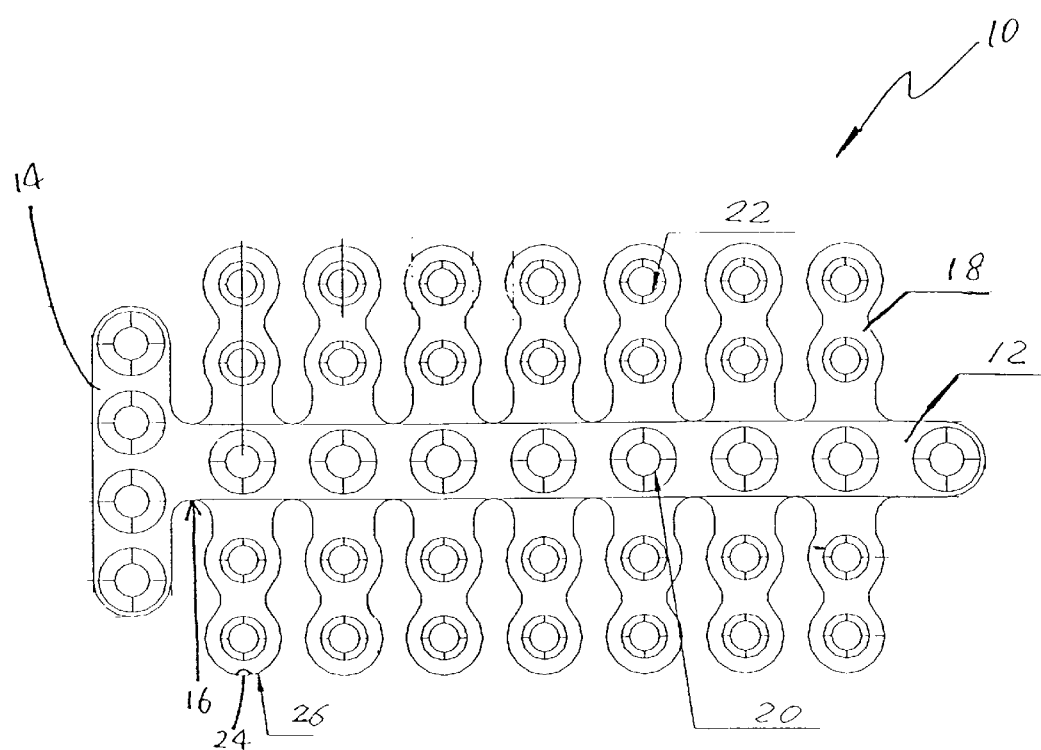

FIXATION DEVICE

FIELD OF THE INVENTION

The present invention relates generally to a fixation device for fixing fractures. In particular, the present invention relates to an orthopaedic fixation device adapted to internally fix comminuted fractures in small bones with a complicated anatomy.

BACKGROUND OF THE INVENTION

Difficult bony fractures are typically treated by open reduction and internal fixation. When a fractured bone is displaced and unstable, an orthopaedic implant is often used to internally stabilize or support the fractured bone. Different types of implants are produced by various companies for fixing fractures in different body parts. Generally, implants can reconstruct a stable bony framework by either load sharing or load shielding to allow the injured body part to be mobilized.

Fracture fixation can, however, become very complicated under a number of situations. When fractures occur in small bones, such as phalangeal bones, fracture fixation is difficult due to the small size of the bones as well as their close relations to multiple soft tissue structures. For small bone fixation, conventional implants can fix fracture fragments with only simple fracture configuration and reasonably large size. Normally, a bony fragment must be three times the size of an implant, such as a screw, in order for the bony fragment to be fixable by the implant. Currently, the smallest available screws for hand fractures have a diameter of 1.3 mm to 1.5 mm. Thus a fixable fragment must be larger than 4 mm. However, in a real life situation, fracture fragments can often be smaller than 4 mm. Consequently, no screws can be used to stabilize such small fragments to allow early mobilization of the injured body part.

Moreover, when comminuted fractures occur, bone collapses, complicated fracture lines, and multiple bone fragments can make fracture fixation much more difficult. Conventional implants can provide only a semi-rigid fracture fixation in cases of comminuted fractures. Due to such an insufficient support and/or fixation for the fractured bones, the mobility of the injured body part has to be sacrificed. Accordingly, conventional implants are inadequate to fix comminuted fractures to allow mobilization of the injured body part for its early rehabilitation.

Therefore, it is desirable to provide a fixation device to address the above problems. The present invention provides such a fixation device that is capable of fixing comminuted fractures, especially in a small bone.

SUMMARY OF THE INVENTION

The present invention provides a fixation device capable of fixing all types of fractures. In particular, the present invention provides a fixation device for internally fixing fractures occurred in small bones, such as phalangeal bones. The fixation device of the present invention comprises an elongated support plate, a transverse plate fixed to and extending transversely from the elongated support plate, and a fin member fixed to and extending transversely from the elongated support plate.

According to the present invention, the elongated support plate and the transverse plate define a plurality of first holes therein for receiving first fixing elements to mount the fixation device onto a bone. The first holes can be so located that the first fixing elements can prevent the fixation device from rotating and/or translating relatively to the bone after the fixation device is mounted onto the bone. Thus, the elongated support plate and the transverse plate can support the injured bone and allow early mobilization of the injured body part, such as neighboring joints of the fractured bone. In addition, the fin member is formed to be more flexible than the transverse plate. Thereby, the fin member can be bent to conform to the contour of the bone for fixing and/or stabilizing a fractured fragment or multiple fractured fragments. As a result, the fixation device can support an injured bone as well as fix or stabilize a fractured fragment or multiple fractured fragments. The fixation device of the present invention is a versatile implant, which can be fixed to any bone of any body part, from a phalangeal to toe bone. In one embodiment, the fixation device is formed to be fixed onto small bones, such as phalangeal bones.

According to an independent and separate aspect of the present invention, the fixation device can be formed so that it can fix or stabilize small fractured fragments. In an exemplary embodiment, the fin member can be formed to stabilize small fracture fragments, such as those under 4 mm. Additionally or alternatively, the fixation device of the present invention can fix different kinds of fractures, from simple to comminuted fractures, while allowing mobilization of the injured body part for its early rehabilitation. In a preferred embodiment, the fixation device can have a plurality of fin members adapted to fix or stabilize multiple fractured fragments, such as in the case of comminuted fractures.

Optionally, the fixation device can be formed to receive additional fixing elements to thereby support fractured fragments and to increase the strength of the fixation device. In one embodiment, the fin member can define a second hole therein for receiving a second fixing element for fixing fractured fragments. In an alternative embodiment, the fin member can have a remote end which defines a cut-out portion thereat for receiving a third fixing element to provide additional support for both the fractured bone and the fixation device.

The fixation device of the present invention can be otherwise formed to minimize the contact area between the fixation device and the bone and/or to decrease soft tissue impingement. In one embodiment, fin members can be removed from the fixation device when such fin members become unessential for fixation.

These and other features and advantages of the present invention will be readily apparent from the following detailed description of the invention, the scope of the invention being set out in the appended claims.

BRIEF DESCRIPTION OF THE DRAWINGS

The detailed description of the present invention will be better understood in conjunction with the accompanying drawing which shows a planar view of a fixation device formed according to the principles of the present invention.

DETAILED DESCRIPTION OF THE EMBODIMENTS

An exemplary fixation device embodying the principles of the present invention is shown in the drawing and will now be described in detail as follows.

The fixation device 10 of the present invention can comprise an elongated support member 12 and a transverse member 14 fixed to each other. The transverse member 14 can extend transversely to the elongated member 12 forming a support frame 16 of the fixation device 10. The support frame 16 can be adapted to mount the fixation device 10 onto an injured bone (not shown) to thus adequately support an injured bone.

The fixation device 10 can also comprise one or more fin members 18 extending transversely from the elongated member 12. The fin members 18 can be formed to be more flexible than the elongated member 12 and/or the transverse member 14. Thus, the fin members 18 can be bent to conform to the contour of the injured bone to fix and/or stabilize the same. Additionally or alternatively, the fin members 18 can be used to fix and/or stabilize a fractured fragment or multiple fractured fragments. In one embodiment, the fin members 18 can be bent to buttress fractured fragments without additional fixing elements, such as screws.

According to the present invention, the support frame 16 can adequately support the injured bone. As a result, the fixation device 10 allows mobilization of the injured body part, which is beneficial for its early rehabilitation. In addition, the fin member 18 of the fixation device 10 can fix or stabilize a fractured and/or displaced fragment. As will be described in greater detail in a latter embodiment, the fixation device 10 can comprise a plurality of fin members 18. Therefore, the fixation device 10 of the present invention can be used for fixing comminuted fractures.

The fixation device 10 of the present invention can be mounted onto the injured bone by various mechanism. As shown in the drawing, the support frame 16 can collectively define a plurality of holes 20 therein for receiving first fixing elements (not shown). For example, the first fixing elements can be screws adapted to be inserted in the holes 20 and pierce into an intact portion of the injured bone to thereby mount the fixation device 10 onto the bone. In one embodiment, the holes 20 can be holes, each of which can be adapted to receive one fixing screw. It will be appreciated that other joining mechanism, such as adhesion, can also be used to mount the fixation device 10 onto the bone and is also within the scope of the present invention.

Optionally, the elongated member 12 and the transverse member 14 can each define two or more holes 20 thereon. For example, the elongated support member 12 can define two to ten holes 20 thereon. In an alternative embodiment, the transverse member 14 can define two to four holes 20 thereon. Additionally or alternatively, the holes 20 can have different spacing in between. Thereby, support frame 16 can be adapted to be mounted onto bones of different sizes and/or different fracture conditions.

As another independent aspect of the present invention, the holes 20 can have various sizes depending on the application of the fixation device 10. Generally, the holes 20 can have a larger dimension when the fixation device 10 is used for fixing fractures occurred in larger bones. In one embodiment where the fixation device 10 is adapted to fix fractures in small bones, such as phalangeal bones, the holes 20 can have a diameter ranging from about 1.3 mm to about 2 mm. In another embodiment, the holes 20 can have a diameter of about 1.7 mm. Optionally, the holes 20 can be formed with a 90 degree countersunk to accommodate screw heads after the fixation device 10 is mounted onto the injured bone. It will be appreciated that other sizes for the holes 20 are also within the scope of the present invention.

Additionally or alternatively, the holes 20 can be so formed that the first fixing elements can prevent the fixation device 10 from rotating and/or translating relatively to the bone after the fixation device 10 is mounted onto the bone. In one embodiment, the elongated support member 12 and the transverse member 14 can collectively define three holes. The holes 20 are so located on the support frame 16 that they are not aligned in the same line. Thereby, when the fixation device 10 is mounted onto the injured bone, the screws can effectively eliminate the fixation device 10 from rotating and/or translating in relation to the bone.

The fixation device 10 can be made of various suitable materials. In one embodiment, the elongated support member 12 and the transverse member 14 can be formed of a substantially rigid material to provide adequate support for the injured bone. An example of a suitable material can be a medical grade stainless steel, which is commonly used in making miniplates or screws. Other exemplary materials applicable for the support member 12 and the transverse member 14 include, but not limited to, titanium, organic materials, and resorbable materials.

The support frame 16 can be formed in various manners to support the injured bone after the fixation device 10 is amounted onto the bone. In the embodiment, the elongated support member 12 and the transverse member 14 can be formed in a plate shape. The elongated support plate 12 and the transverse plate 14 can have a thickness within any range suitable for internal fracture fixation. In one embodiment, the thickness of the plates 12 and 14 can range from about 0.4 mm to about 1.0 mm and preferably 0.6 mm to 0.9 mm. In another embodiment, the thickness of the plates 12 and 14 can be about 0.8 mm. According to one aspect of the present invention, the thickness of the plates 12 and 14 is larger than that of the fin member 18 as will be described later.

The elongated plate 12 and the transverse plate 14 can each have a length and a width determined based on the application of the fixation device 10. Generally, the elongated support plate 12 can have such a length that the plate 12 can sufficiently span an injured portion of the bone for supporting the same. In one embodiment, the length of the elongated plate 12 can range from about 10 mm to about 50 mm. On the other hand, the transverse plate 14 can have a length for mounting to bones of different sizes. In one embodiment, the length of the transverse plate 14 can range from about 8 mm to about 16 mm. Additionally or alternatively, both the elongated support plate 12 and the transverse plate 14 can have a similar width in any suitable range. In one embodiment, the width of the plates 12 and 14 can range from about 3.5 mm to about 4.0 mm. It will be appreciated that other suitable length and width of the elongated plate 12 and the transverse plate 14 are also within the scope of the present invention.

Optionally, the elongated support plate 12 and/or the transverse plate 14 can be slightly bent to conform to the injured bone and to facilitate fracture reduction before the fixation device 10 is mounted onto the bone. For example, the transverse member 14 can be bent to conform to the contour of one end of the injured bone before being mounted thereon. In one embodiment, the transverse member 14 can be bent to conform to either the proximal end or the distal end of a phalangeal bone. Additionally or alternatively, the elongated support member 12 and the transverse member 14 can be pre-deformed to conform to the specific configuration of a particular bone.

In one embodiment, the transverse member 14 is fixed to one end of the elongated member 12 so that the support frame 16 assumes a T-shape. It will be appreciated that the elongated member 12 and the transverse member 14 can join to each other to form other shapes, such as an L-shape and a cross shape. It will also be appreciated that the elongated member 12 and the transverse member 14 can cross with each at various angles other than 90 degrees.

In the exemplary embodiment, the fixation device 10 can have a plurality of fin members 18 transversely extending from the elongated support member 12. For example, seven pairs of fin members 18 can be provided and located on both sides of the elongated support member 12. Each fin member 18 can be adapted to fix and stabilize a displaced fragment. As a result, the fixation device 10 can fix multiple fractured fragments, such as in the case of comminuted fractures.

According to the present invention, each fin member 18 can be formed so that it can be adapted to conform to the shape of the injured bone. In one embodiment, the fin members 18 can be formed so that they can have a smaller thickness than that of the transverse plate 14. For example, the thickness of the fin members can range from about 0.3 mm to 0.5 mm, preferably 0.4 mm. As a result, the fin members 18 can be readily bent or otherwise deformed to circumscribe the entire cortex of the injured bone to support the fractured fragments. The fin members 18 thus serve as a buttressing device for fracture fragments to thereby improve the strength of the internal fixation. In one embodiment, the fin members 18 can thus assist in fixing comminuted bone fractures where small fracture fragments, such as those of 4 or 5 mm or less, make a screw fixation impossible. In another embodiment, the fin members 18 can be pre-bent to conform to the shape of the injured bone. The fin members 18 so formed can aid fracture reduction to restore the original shape and height of the injured bone, even when the fracture is as comminuted as a collection of loose bony fragments.

Additionally or alternatively, each fin member 18 can define at least one hole 22 therein for receiving a second fixing element (not shown) to provide additional fixation for the fragments. The holes 22 can be formed in various manners to fix a variety of fractures. In an exemplary embodiment, such as shown in the drawing, the holes 22 can be provided on the fin members 18 dorsally or laterally along the entire length thereof to receive the second fixing elements, such as screws, in the best available positions. Depending on the fracture situation, one or more holes 22 on the same or different fin members 18 can be provided for mounting the fractured fragments in the most appropriate manner. Generally, when more screws are used, the strength of the whole fixation can be increased. Therefore, multiple holes 22 in the fin members 18 make it possible to improve the fixation strength of the fixation device 10, especially the torsional strength. As a result, the fixation device 10 of the present invention is capable of solving the problem of fixing difficult fractures, such as very comminuted fractures.

In an exemplary embodiment, each fin member 18 can define two holes 22 therein for receiving screws for fixing a bony fragment of an adequate size. This is particularly advantageous for very comminuted fractures of small bones, such as phalangeal bones, where the intact part of the bone may not fit exactly with the positions of the holes 20 on the support frame 16. The size of the holes 22 on each fin member 18 can vary depending on the fracture situation. In one embodiment, the holes 22 can have a diameter in the range of 1.3 mm to 1.8 mm, preferably 1.5 mm. Optionally, the holes 22 can be formed with a 90 degree countersunk to accommodate screw heads when the fixation device 10 is mounted onto the bone.

According to another aspect of the present invention, the fixation device 10 can comprise a plurality of cut-out portions 24 formed at the remote end 26 of the fin members 18. The cut-out portions 24 can allow the fin members 18 to be tied up by using third fixing element, such as a surgical suture in a manner like threading a shoe. The suture can be tied into the part of the bone and thereby assist in holding the fragments where screw fixation is impossible or inadequate. The suture can be made to pass through the holes 22 without any additional aid to therefore significantly reduce the required operation time and to allow threading in awkward positions.

In one embodiment, the cut-out portions 24 can be oriented differently with respect to the axis of holes 22. As a result, the suture can pull opposite or adjacent fin members 18 together to increase the fixation strength. In another embodiment, the suture can circumscribe the entire bone to provide extra strength. When the suture is given sufficient tension, the fixation device 10 together with the fractured phalangeal bone inside can form a composite body, which is much stronger than that formed with conventional dorsal or lateral plates. It will be appreciated that other embodiments for strengthening the fixation are also within the scope of the present invention.

The fixation device 10 of the present invention can be found in various manners to allow blood vessels to grow into the injured bone. For example, the fixation device 10 can be formed as an open structure to reduce soft tissue disturbance and minimize the total amount of foreign materials implanted in the injured body part. In one embodiment, the fin members 18 can be removably formed on the support frame 16. Accordingly, when a fin member 18 is considered not essential for a fracture fixation, such a fin member 18 can be easily cut away or otherwise removed to minimize the amount of foreign materials inside a body part, such a digit. In another embodiment, the total bone contact area can be minimized by removing a portion of the fin member 18. The reduced portion of the fin member 18 can further facilitate an easy or smooth bending of the fin member 18. Additionally or alternatively, only an adequate but not excess number of screws will be used to minimize soft tissue stripping of the bone. It will be appreciated that other methods for reducing the total bone contact area are also within the scope of the present invention.

Additionally or alternatively, all edges of the fixation device 10 can be rounded. Accordingly, after being mounted onto the injured bone, the fixation device 10 will not hinder tendons sliding over the fixation device 10. This is especially important in phalangeal fracture reduction as an early movement of the injured finger can be essential for good final outcome.

The fixation device 10 of the present invention can be especially useful for very comminuted fractures in small bones with complicated anatomy. The holes 22 on the fin members 18 and the cut-out portions thereon can provide adequate receiving mechanism for fixing elements, such as screws, and sutures, to thereby form a buttressing unit for very comminuted bony fragments. An adequate number of fixing elements, such as screws, can be used to be mounted onto the intact portions of the injured bone even at awkward positions. Additionally or alternatively, additional fixation elements, such as sutures, can be tied to the fin members 18 at their cut-out portions to improve the strength of the whole fixation. As a result, the fixation device 10 of the present invention can provide a rigid internal fixation.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being indicated by the appended claims, and not limited to the foregoing description.

What is claimed is:

1. A fixation device for internally fixing fractures, comprising:

an elongated support plate;

a transverse plate fixed to and extending transversely from the elongated support plate; and a fin member fixed to and extending transversely from the elongated support plate;

wherein the elongated support plate, the transverse plate, and the fin member extend in the same plane;

wherein the elongated support plate and the transverse plate define a plurality of first holes therein for receiving first fixing elements to mount the fixation device onto a bone, the first holes being so located that the first fixing elements can prevent the fixation device from rotating relatively to the bone after the fixation device being mounted onto the bone; and wherein the fin member is more flexible than the transverse plate so that the fin member can be bent to conform to the contour of the bone for fixing the fractures.

2. The fixation device of claim 1, wherein the elongated support plate and the fin member each have a first and a second thickness, respectively, and wherein the first thickness is larger than the second thickness.

3. The fixation device of claim 1, wherein there are a plurality of fin members extending on opposite sides of the elongated support member.

4. The fixation device of claim 3, wherein there are a plurality of fin members extending on the same side of the elongated support member.

5. The fixation device of claim 1, wherein the fin member defines a second hole therein for receiving a second fixing element to fix a fractured bone.

6. The fixation device of claim 1, wherein the fin member defines a plurality of second holes therein.

7. The fixation device of claim 5, wherein the first and second holes are circular and each have a diameter of less than about 2 mm.

8. The fixation device of claim 5, wherein the first and second holes are circular and each have a diameter ranging from about 1.3 mm to about 2 mm.

9. The fixation device of claim 8, wherein each first hole has a diameter of about 1.7 mm.

10. The fixation device of claim 8, wherein the second hole has a diameter ranging from about 1.3 mm to about 1.5 mm.

11. The fixation device of claim 8, wherein the second hole has a diameter of about 1.3 mm.

12. The fixation device of claim 6, wherein the first holes have a larger dimension than the second hole.

13. The fixation device of claim 3, wherein the fin members each have at least one remote end and wherein each remote end comprises a cut-out portion for accommodating a third fixing element to provide further support for fractured bones.

14. The fixation device of claim 1, wherein the transverse plate comprises a plurality of first holes for mounting the fixation device to differently sized bones.

15. The fixation device of claim 1, wherein the elongated support plate comprising two ends and wherein the transverse plate is fixed to one of the two ends for mounting onto one end of the bone.

16. The fixation device of claim 3, wherein the fin members are removable from the elongated support plate to minimize the total contact area between the fixation device and the bone.

17. The fixation device of claim 6, wherein the fin members have a reduced portion between adjacent second holes to minimize the total contact area between the fixation device and the bone and to facilitate smooth bending of the fin members.

18. The fixation device of claim 1, wherein the elongated support plate, the transverse plate, and the fin member each have at least one remote end, and wherein the remote ends are rounded to form a smooth contour of the fixation device.

19. A fixation device for internally fixing fractures, comprising:

first and second support plates transversely fixed to each other;

a plurality of fin members fixed to and extending transversely from at least one of the support plates;

wherein the first and second support plates define a plurality of first holes therein for receiving fixing elements to mount the fixation device onto a bone, the first holes being so located that the fixing elements can prevent the fixation device from rotating relatively to the bone after the fixation device being mounted onto the bone; and wherein the fin members are more flexible than either the first or the second plate so that the fin members can be bent to conform to the contour of the bone for fixing the fractures.

* * * * *